US008557969B2

(12) United States Patent
Metzger et al.

(10) Patent No.: US 8,557,969 B2
(45) Date of Patent: Oct. 15, 2013

(54) COMPOSITIONS AND METHODS FOR REGULATING CARDIAC PERFORMANCE

(75) Inventors: Joseph Metzger, Ann Arbor, MI (US); Margaret Westfall, Ann Arbor, MI (US); Sharlene Day, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1017 days.

(21) Appl. No.: 11/792,216

(22) PCT Filed: Dec. 1, 2005

(86) PCT No.: PCT/US2005/043584
§ 371 (c)(1),
(2), (4) Date: Jun. 2, 2008

(87) PCT Pub. No.: WO2007/046826
PCT Pub. Date: Apr. 26, 2007

(65) Prior Publication Data
US 2008/0263691 A1 Oct. 23, 2008

Related U.S. Application Data

(60) Provisional application No. 60/632,157, filed on Dec. 1, 2004.

(51) Int. Cl.
*C07H 21/02* (2006.01)
(52) U.S. Cl.
USPC ........................................ 536/23.1; 514/44 R
(58) Field of Classification Search
USPC ........................................ 536/23.1; 514/44 R
See application file for complete search history.

(56) References Cited

U.S. PATENT DOCUMENTS

| | | | |
|---|---|---|---|
| 5,994,132 A | 11/1999 | Chamberlain et al. | |
| 6,057,158 A | 5/2000 | Chamberlain et al. | |
| 6,063,622 A | 5/2000 | Chamberlain et al. | |
| 6,083,750 A | 7/2000 | Chamberlain et al. | |
| 6,451,596 B1 | 9/2002 | Chamberlain et al. | |
| 6,686,200 B1 * | 2/2004 | Dong et al. | 435/457 |
| 7,078,486 B2 | 7/2006 | Shi et al. | |
| 7,393,829 B2 | 7/2008 | Moses et al. | |
| 2003/0100526 A1 | 5/2003 | Souza et al. | |

OTHER PUBLICATIONS

Printout from http://www.ncbi.nlm.nih.gov/nuccore/BC100590.1?ordinalpos=6&itool=EntrezSystem2.PEntrez.Sequence, pp. 1-3, printed Feb. 8, 2010.*
Westfall et al. Circ Res 86:470-477, 2000.*
Braunwald and Kloner, 1982, "The stunned myocardium: prolonged, postischemic ventricular dysfunction", Circulation 66:1146.
Coutu and Metzger, 2002, "Optimal range for parvalbumin as relaxing agent cardiac myocytes: gene transfer and mathematical modeling", Biophys J 82:2565.
Coutu et al., 2004, "Parvalbumin corrects slowed relaxation in adult cardiac myocytes expressing hypertrophic cardiomyopathy-linked alpha-tropomyosin mutations", Circ Res 94:1235.
Del Monte et al., 2004, "Abrogation of ventricular arrhythmias in a model of ischemia and reperfusion by targeting myocardial calcium cycling", Proc Natl Acad Sci 101:5622.
Fentzke et al., 1999, "impaired cardiomyocyte relaxation and diastolic function in transgenic mice expressing slow skeletal troponin I in the heart", J Physiol. May 15, 1999; 517 (Pt 1):143-57.
Gao et al., 1996, "Intrinsic myofilament alterations underlying the decreased contractility of stunned myocardium. A consequence of Ca2+ -dependent proteolysis?" Circ Res 78:455.
Gasmi-Seabrook et al., 1999, "Solution structures of the C-terminal domain of cardiac troponin C free and bound to the N-terminal domain of cardiac troponin I." Biochemistry Oct. 26, 1999;38(43):14432.
Hofmann et al., 1993, "Altered calcium sensitivity of isometric tension in myocyte-sized preparations of porcine postischemic stunned myocardium", Circ Res 72:50.
Hunkeler et al., 1991, "Troponin I isoform expression in human heart", Circ Res, 69:1409.
Knot et al., 2003, "Prognostic importance of physical examination for heart failure in non-ST-elevation acute coronary syndromes: the enduring value of Killip classification", JAMA 290:2174.
Kiuchi et al., 1993, "Myocardial beta-adrenergic receptor function during the development of pacing-induced heart failure", J Clin Invest 91.907.
Lee and Allen, 1991, "Mechanisms of acute ischemic contractile failure of the heart. Role of intracellular calcium", J Clin Invest, 88:361.
Metzger et al., 2004, "Covalent and noncovalent modification of thin filament action: the essential role of troponin in cardiac muscle regulation", Circ Res. Feb. 6, 2004;94(2):146-58.
Michele et al., 2002, "Cardiac dysfunction in hypertrophic cardiomyopathy mutant tropomyosin mice is transgene-dependent, hypertrophy-independent, and improved by beta-blockade", Circ Res 91:255.
Murphy, 2002, "Troponin I: in sickness and in health-and normal development", Circ Res. Sep. 20, 2002;91(6):449-50.
Orchard and Kentish, 1990, "Effects of changes of pH on the contractile function of cardiac muscle", Am J Physiol, 258:C967.
Piper et al., 2003, "Cellular mechanisms of ischemia-reperfusion injury", Ann Thorac Surg 75: S644.
Solaro and Rarick, 1998, "Troponin and tropomyosin: proteins that switch on and tune in the activity of cardiac myofilaments", Circ Res, 83:471.
Solaro et al., 1988, "Effects of acidosis on ventricular muscle from adult and neonatal rats", Circ Res, 63:779.
Steenbergen et al., 1990, "Correlation between cytosolic free calcium, contracture, ATP, and irreversible ischemic injury in perfused rat heart", Circ Res 66:135.

(Continued)

Primary Examiner — Marcia S Noble
(74) Attorney, Agent, or Firm — Casimir Jones SC

(57) ABSTRACT

The present invention relates to cardiac performance, in particular to regulating cardiac performance via recombinant troponin I (TnI) protein and nucleic acids encoding recombinant TnI. The present invention provides nucleic acids encoding gain of function TnI proteins (e.g., cTnIA164H), vectors containing such nucleic acids, host cells containing such vectors, transgenic animals carrying a gain of function TnI protein (e.g., a cTnIA164H transgene), and therapeutic agents (e.g., comprising recombinant TnI, TnI analogues, synthetic TnI, or the like) or agents for gene therapy of heart failure or disease for research and therapeutic uses.

3 Claims, 4 Drawing Sheets

(56) References Cited

OTHER PUBLICATIONS

Steg, et al., 2004, "Determinants and prognostic impact of heart failure complicating acute coronary syndromes: observations from the Global Registry of Acute Coronary Events (GRACE)." Circulation 109:494.

Szatkowski et al., 2001, "In vivo acceleration of heart relaxation performance by parvalbumin gene delivery", J Clin Invest 107:191.

Takeda et al., 2003, "Structure of the core domain of human cardiac troponin in the Ca(2+)-saturated form", Nature 424:35.

Tripet et al., 1997, "Mapping of a second actin-tropomyosin and a second troponin C binding site within the C terminus of troponin I, and their importance in the Ca2+-dependent regulation of muscle contraction", J Mol Biol 271:728.

Varma et al., 2003, "Mechanisms underlying ischemic diastolic dysfunction: relation between rigor, calcium homeostasis, and relaxation rate", Am J Physiol 284:H758.

Westfall and Metzger, 2001, "Troponin I isoforms and chimeras: tuning the molecular switch of cardiac contraction", News Physiol Sci 16:278.

Westfall et al., 1998, Meth Cell Biol 32:307-322.

Westfall et al., 1999, "Functional analysis of troponin I regulatory domains in the intact myofilament of adult single cardiac myocytes", J Biol Chem 274:22508.

Westfall et al,, 2000, "Chimera analysis of troponin I domains that influence Ca(2+)-activated myofilament tension in adult cardiac myocytes", Circ Res 86:470.

Westfall et al., 2001, "Troponin I chimera analysis of the cardiac myofilament tension response to protein kinase A", Am J Cell Physiol, 280:C324.

Westfall et al., 2002, "Myofilament calcium sensitivity and cardiac disease: insights from troponin I isoforms and mutants", Circ Res 91:525.

* cited by examiner

US 8,557,969 B2

COMPOSITIONS AND METHODS FOR REGULATING CARDIAC PERFORMANCE

CROSS-REFERENCE TO RELATED APPLICATIONS

This application is a U.S. National Phase Entry of International Patent Application No. PCT/US2005/043584, international filing date Dec. 1, 2005, which claims priority to expired U.S. Provisional Patent Application No. 60/632,157, filed Dec. 1, 2004, the contents of which are incorporated by reference in their entireties.

This invention was funded, in part, under NIH grant HL059301. The government may have certain rights in the invention.

FIELD OF THE INVENTION

The present invention relates to cardiac performance, in particular to regulating cardiac performance via recombinant troponin I (TnI) protein and nucleic acids encoding recombinant TnI. The present invention provides nucleic acids encoding gain of function TnI proteins (e.g., cTnIA164H), vectors containing such nucleic acids, host cells containing such vectors, transgenic animals carrying a gain of function TnI protein (e.g., a cTnIA164H transgene), and therapeutic agents (e.g., comprising recombinant TnI, TnI analogues, synthetic TnI, or the like) or agents for gene therapy of heart failure or disease for research and therapeutic uses.

BACKGROUND OF THE INVENTION

Ischemic heart disease and failure is a leading cause of mortality worldwide, accounting for 6.9 million deaths in the year 2000 (See, e.g., Michaud et al., JAMA 285:535 (2001)). Heart failure can result from any condition that reduces the ability of the heart to pump blood. Most frequently, heart failure is caused by decreased contractility of the myocardium, resulting from reduced coronary blood flow. Many other factors may result in heart failure, including damage to the heart valves, vitamin deficiency, and primary cardiac muscle disease (See, e.g., Guyton, Human Physiology and Mechanisms of Disease, Third Edition, W. B. Saunders Co., Philadelphia, Pa., 205 (1982)). Heart failure is commonly manifested in association with myocardial infarction. (See, e.g., Dunagan and Ridner, Manual of Medical Therapeutics, Twenty-Sixth Edition, Little, Brown & Co., Boston, 106 (1989)).

The precise physiological mechanisms of heart failure are not entirely understood. However, heart failure is generally believed to involve disorders in several cardiac autonomic properties, including sympathetic, parasympathetic, and baroreceptor responses. (See, e.g., K. Kiuchi et al. (1993) J. Clin. Invest. 91:907).

Myocardial ischemia and infarction cause a precipitous decline in contractile function, which can lead to acute congestive heart failure. Despite major advances in early reperfusion and revascularization strategies, heart failure remains a common complication of acute coronary syndromes and a powerful predictor of mortality (See, e.g., Khot et al., JAMA 290:2174 (2003); Steg et al., Circ 109:494 (2004)). Myocardial contractile dysfunction during ischemia is due, in no small part, to the effects of intracellular acidosis on the contractile machinery. Acidosis directly depresses myocardial force production despite unchanged or increased levels of intracellular calcium (See, e.g., Orchard and Kentish Am J Physiol 258:C967 (1990)). One mechanism responsible for this pH-mediated force decrement is a decrease in the calcium responsiveness of the contractile myofilaments (See, e.g., Orchard and Kentish Am J Physiol 258:C967 (1990); Lee and Allen J Clin Invest 88:361 (1991)). Current methods of treating the heart during heart failure do not render cardiac muscle resistant to the detrimental effects of acidosis and fail to re-sensitize the contractile machinery to calcium signaling.

Therefore, what is needed is a treatment for the heart (e.g., contractile myofilaments) that protects and augments the hearts ability to respond to calcium during ischemia-induced pH changes. Furthermore, better models (e.g., animal models) are needed in order to study the heart's response to calcium signalling while under oxygen deprivation conditions.

SUMMARY OF THE INVENTION

The present invention relates to cardiac performance, in particular to regulating cardiac performance via recombinant troponin I (TnI) protein and nucleic acids encoding recombinant TnI. The present invention provides nucleic acids encoding gain of function TnI proteins (e.g., cTnIA164H), vectors containing such nucleic acids, host cells containing such vectors, transgenic animals carrying a gain of function TnI protein (e.g., a cTnIA164H transgene), and therapeutic agents (e.g., comprising recombinant TnI, TnI analogues, synthetic TnI, or the like) or agents for gene therapy of heart failure or disease for research and therapeutic uses.

Accordingly, in some embodiments, the invention provides an isolated nucleic acid sequence that encodes a gain of function troponin I (TnI) protein. In some embodiments, the gain of function TnI protein possesses an amino acid substitution of histidine for alanine. In some embodiments, the gain of function TnI protein possesses a natural or synthetic charged amino acid substituted for alanine. In a preferred embodiment, the invention provides a recombinant expression vector comprising a nucleic acid sequence that encodes a gain of function TnI protein, the protein having an amino acid substitution of histidine for alanine, or other natural or synthetic charged amino acid. In some embodiments, the expression vector is contained within a host, host tissue or host cell. In further embodiments, the expression vector is an adenoviral vector or an adeno-associated vector (See, e.g., U.S. Pat. Nos. 6,451,596, 6,083,750, 6,063,622, 6,057,158, or 5,994,132, all of which are herein incorporated by reference).

In some embodiments, the invention provides a method for expressing gain of function cTnI proteins comprising: providing: i) a recombinant virus comprising a gain of function cTnI nucleic acid encoding a gain of function cTnI protein, and ii) a host, host tissue or cultured host cells; and introducing the recombinant viruses into the host, host tissue or cultured host cells, whereby the recombinant viruses transduce the host, host tissue or cultured host cells.

In some embodiments, the invention provides an isolated mammalian host cell containing a recombinant expression vector comprising a nucleic acid sequence that encodes a gain of function TnI protein, the gain of function cTnI protein having an amino acid substitution of histidine for alanine, wherein the isolated mammalian host cell is selected from the group consisting of (a) a cardiac cell, and (b) a mouse cell, the mouse cell selected from the group consisting of an embryonic stem cell, an eight-cell embryo cell, a blastocoele cell, and a blastomere cell. In some embodiments, the isolated mammalian host cell is a mouse fertilized egg cell. In some embodiments, the expression vector comprises a promoter sequence. In some embodiments, the promoter sequence is the α-myosin heavy chain promoter.

In some embodiments, the invention provides a method of expressing gain of function cTnI in a mammal, comprising: a) providing i) a mammalian cell selected from the group consisting of an embryonic stem cell, an eight-cell embryo cell, a blastocoele cell, and a fertilized egg cell; ii) a nucleic acid sequence encoding gain of function cTnI; iii) a promoter sequence; and iv) a female host mammal; b) operably linking the nucleic acid sequence encoding gain of function cTnI and the promoter sequence to produce a transgene; c) introducing the transgene into the mammalian cell to create a treated cell; d) introducing the treated cell into the female host mammal under conditions such that the female host mammal delivers a progeny wherein the transgene is integrated into the somatic and germ cells of the progeny, and wherein the progeny expresses the gain of function cTnI protein in a cardiac cell.

In some embodiments, the invention provides a transgenic animal carrying a gain of function cTnI transgene under the control of a promoter sequence, wherein the gain of function cTnI transgene is expressed in cardiac cells. In some embodiments, the promoter sequence is the α-myosin heavy chain promoter. In some embodiments, the transgenic animal is a mouse, rat, cow, horse, dog, pig, cat, rabbit, or a monkey.

In some embodiments, the invention provides a method for treating a host, comprising: a) providing: i) a recombinant expression vector comprising a gain of function cTnI nucleic acid sequence; and ii) a host cell; and b) introducing the vector into the host cell under conditions such that the host cell expresses the gain of function cTnI nucleic acid sequence wherein the sequence encodes a gain of function cTnI protein. The above methods find use in research, drug screening and therapeutic applications.

In some embodiments, the invention provides a method for treating a host, comprising: a) providing: i) a gain of function TnI protein (e.g., a gain of function recombinant TnI, TnI analogue, synthetic TnI, chimeric molecule comprising gain of function TnI); and ii) a host cell; and b) introducing the gain of function TnI protein to the host cell. The above methods find use in research, drug screening and therapeutic applications.

DEFINITIONS

Figure 1:
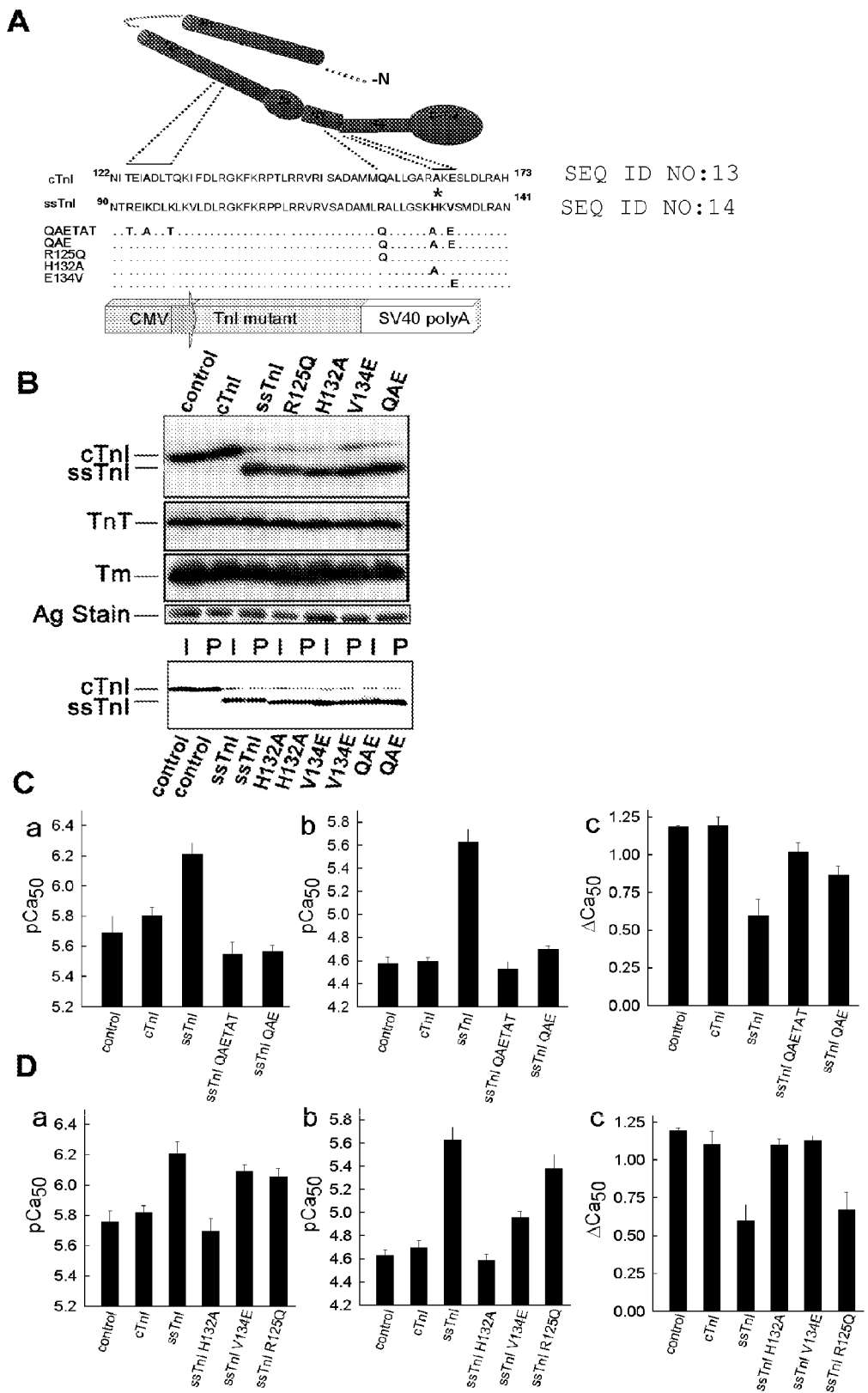
FIG. 1 shows that a single amino acid confers differential pH sensitivity in slow skeletal and cardiac troponin I isoforms.

To facilitate an understanding of the present invention, a number of terms and phrases are defined below:

As used herein, the terms "gain of function cTnI protein," "gain of function cTnI nucleic acid," "gain of function mutant," "gain of function nucleic acids," "gain of function amino acid substitution" and "gain of function proteins" refer to mutant nucleic acids and mutant TnI proteins wherein, for example, a natural or synthetic charged amino acid is substituted for a conserved alanine found in the pH sensitive domain of the C-terminus of the TnI protein, such that the gain of function mutant functions in vivo to preserve contractile force during ischemic events, reperfusion injury or other damage to cardiac tissue. For example, one gain of function mutant of the present invention is a substitution replacing alanine at position 164 in the mouse cTnI protein with a natural or synthetic charged amino acid, and nucleic acids encoding the same. Other mutants encompassed by the present invention are homologues of the mouse mutant. These include substitutions replacing alanine at position 164 in the rat, cow, dog and rabbit cTnI protein, substitution replacing alanine at position 163 in the monkey, human and cat, and substitution replacing alanine at position 158 in the horse, and nucleic acids encoding the same. Other functional equivalents are also encompassed. Such functional equivalents are readily selected by detecting gain of function.

The term "myocyte" refers to muscle cells that are characterized by containing myosin. The term "cardiac myocyte" refers to cells containing myosin which are located in or isolated from the myocardium.

The term "in vitro culture" refers to the propagation of cellular material outside of its natural environment.

The term "intracellular concentration," when used in reference to a protein or calcium ions, refers to the amount of protein or calcium ions in a cell.

The term "agonist," as used herein, refers to a molecule which, when interacting with an biologically active molecule, causes a change (e.g., enhancement) in the biologically active molecule, which modulates the activity of the biologically active molecule. Agonists may include proteins, nucleic acids, carbohydrates, or any other molecules which bind or interact with biologically active molecules. For example, agonists can alter the activity of gene transcription by interacting with RNA polymerase directly or through a transcription factor.

The terms "antagonist" or "inhibitor," as used herein, refer to a molecule which, when interacting with a biologically active molecule, blocks or modulates the biological activity of the biologically active molecule. Antagonists and inhibitors may include proteins, nucleic acids, carbohydrates, or any other molecules that bind or interact with biologically active molecules. Inhibitors and antagonists can effect the biology of entire cells, organs, or organisms (e.g., an inhibitor that slows neuron degeneration).

The term "modulate," as used herein, refers to a change in the biological activity of a biologically active molecule. Modulation can be an increase or a decrease in activity, a change in binding characteristics, or any other change in the biological, functional, or immunological properties of biologically active molecules.

The term "gene" refers to a nucleic acid (e.g., DNA) sequence that comprises coding sequences necessary for the production of a polypeptide or precursor (e.g., TnI). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mNRA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences which direct the termination of transcription, post-transcriptional cleavage and polyadenylation.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. The term "mutant TnI proteins" refer to TnI proteins with amino acid modifications (e.g., as described in FIGS. 2 and 3).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (See, e.g., Maniatis et al., Science 236:1237 (1987)). Promoter and enhancer elements have been isolated from a variety of eukaryotic sources including genes in yeast, insect and mammalian cells, and viruses (analogous control elements, i.e., promoters and enhancers, are also found in prokaryote). The selection of a particular promoter and enhancer depends on what cell type is to be used to express the protein of interest. Some eukaryotic promoters and enhancers have a broad host range while others are functional in a limited subset of cell types (See, e.g., Voss et al., Trends Biochem. Sci., 11:287 (1986); and Maniatis et al., supra). For example, the SV40 early gene enhancer is very active in a wide variety of cell types from many mammalian species and has been widely used for the expression of proteins in mammalian cells (See, e.g., Dijkema et al., EMBO J. 4:761 (1985)). Two other examples of promoter/enhancer elements active in a broad range of mammalian cell types are those from the human elongation factor 1α gene (See, e.g., Uetsuki et al., J. Biol. Chem., 264:5791 (1989); Kim et al., Gene 91:217 (1990); and Mizushima and Nagata, Nuc. Acids. Res., 18:5322 (1990)) and the long terminal repeats of the Rous sarcoma virus (See, e.g., Gorman et al., Proc. Natl. Acad. Sci. USA 79:6777 (1982)) and the human cytomegalovirus (See, e.g., Boshart et al., Cell 41:521 (1985)). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (See, e.g., Sambrook et al., Molecular Cloning: A Laboratory Manual, 2nd ed., Cold Spring Harbor Laboratory Press, New York (1989), pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (See, e.g., Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to 104 copies/cell) in cells that express the appropriate viral T antigen. Vectors that contain the replicons from bovine papillomavirus or Epstein-Barr virus replicate extrachromosomally at "low copy number" (~100 copies/cell).

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See, e.g., Kacian et al., Proc. Natl. Acad. Sci. USA 69:3038 (1972)). Other nucleic acid will not be replicated by this amplification enzyme. Similarly, in the case of T7 RNA polymerase, this amplification enzyme has a stringent specificity for its own promoters (See, e.g., Chamberlin et al., Nature 228:227 (1970)). In the case of T4 DNA ligase, the enzyme will not ligate the two oligonucleotides or polynucleotides, where there is a mismatch between the oligonucleotide or polynucleotide substrate and the template at the ligation junction (See, e.g., Wu and R. B. Wallace, Genomics 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (See, e.g., Erlich (ed.), PCR Technology, Stockton Press (1989)).

As used herein, the term "antisense" is used in reference to DNA or RNA sequences that are complementary to a specific DNA or RNA sequence (e.g., mNRA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mNRA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

The term "recombinant DNA molecule" as used herein refers to a DNA molecule that is comprised of segments of DNA joined together by means of molecular biological techniques. For example, "recombinant DNA vector" refers to DNA sequences containing a desired coding sequence and appropriate DNA sequences necessary for the expression of the operably linked coding sequence in a particular host organism.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Embryonal cells at various developmental stages can be used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1-2 picoliters (pl) of DNA solution. The use of zygotes as a target for gene transfer has a major advantage in that in most cases the injected DNA will be incorporated into the host genome before the first cleavage (See, e.g., Brinster et al., Proc. Natl. Acad. Sci. USA 82:4438-4442 (1985)). As a consequence, all cells of the transgenic non-human animal will carry the incorporated transgene. This will, in general, also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873,191 describes a method for the micro-injection of zygotes; the disclosure of this patent is incorporated herein in its entirety.

Retroviral infection can also be used to introduce transgenes into an animal. The developing embryo can be cultured in vitro to the blastocyst stage. During this time, the blastomeres can be targets for retroviral infection (See, e.g., Janenich, Proc. Natl. Acad. Sci. USA 73:1260-1264 (1976)). Efficient infection of the blastomeres is obtained by enzymatic treatment to remove the zona pellucida (See, e.g., Hogan et al., in Manipulating the Mouse Embryo, Cold Spring Harbor Laboratory Press, Cold Spring Harbor, N.Y. (1986)). The viral vector system used to introduce the transgene is typically a replication-defective retrovirus carrying the transgene (See, e.g., Jahner et al., Proc. Natl. Acad. Sci. USA 82:6927-693 (1985)). Transfection is easily and efficiently obtained by culturing the blastomeres on a monolayer of virus-producing cells (See, e.g., Van der Putten, supra; Stewart, et al., EMBO J. 6:383-388 (1987)). Alternatively, infection can be performed at a later stage. Virus or virus-producing cells can be injected into the blastocoele (See, e.g., Jahner et al., Nature 298:623-628 (1982)). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (See, e.g., Jahner et al., supra (1982)). Additional means of using retroviruses or retroviral vectors to create transgenic animals known to the art involves the micro-injection of retroviral particles or mitomycin C-treated cells producing retrovirus into the perivitelline space of fertilized eggs or early embryos (See, e.g., PCT International Application WO 90/08832 (1990), and Haskell and Bowen, Mol. Reprod. Dev., 40:386 (1995)).

A third type of target cell for transgene introduction is the embryonal stem (ES) cell. ES cells are obtained by culturing pre-implantation embryos in vitro under appropriate conditions (See, e.g., Evans et al, Nature 292:154-156 (1981); Bradley et al., Nature 309:255-258 (1984); Gossler et al., Proc. Acad. Sci. USA 83:9065-9069 (1986); and Robertson et al., Nature 322:445-448 (1986)). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (See, e.g., Jaenisch, Science 240:1468-1474 (1988)). Prior to the introduction of transfected ES cells into the blastocoel, the transfected ES cells may be subjected to various selection protocols to enrich for ES cells that have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

"Cardiac-specific expression" refers to the expression of mRNA, preferentially in cardiac tissue of animals harboring a gene as compared to other cells or tissue or as compared to a transgenic animal versus a non-transgenic animal lacking the gene or gene expression in its cardiac tissue.

The terms "overexpression" and "overexpressing" and grammatical equivalents, are used in reference to levels of mNRA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (See, e.g., Graham and van der Eb, Virol., 52:456 (1973)), has been modified by several groups to optimize conditions for particular types of cells. The art is well aware of these numerous modifications.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene that is used in conjunction with tk$^-$ cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook, et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "test compound" refers to any chemical entity, pharmaceutical, drug, and the like that can be used to treat or prevent a disease, illness, sickness, or disorder of bodily function. Test compounds comprise both known and potential therapeutic compounds. A "known therapeutic compound" refers to a therapeutic compound that has been shown (e.g., through animal trials or prior experience with administration to humans) to be effective in such treatment or prevention.

As used herein, the terms "host," "expression host," and "transformant" refer to organisms and/or cells which harbor an exogenous DNA sequence (e.g., via transfection), an expression vector or vehicle, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host.

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequalae associated with heart failure, such as shortness of breath, pitting edema, an enlarged tender liver, engorged neck veins, pulmonary rates and the like including laboratory findings associated with heart failure.

The term "treatment" or grammatical equivalents encompasses the improvement and/or reversal of the symptoms of heart failure (e.g., the ability of the heart to pump blood). "Improvement in the physiologic function" of the heart of the non-human transgenic animals of the present invention may be assessed using any of the measurements described herein (e.g., measurement of ejection fraction, fractional shortening, left ventricular internal dimension, heart rate, etc. in response to isoproterenol and/or norepinephrine), as well as any effect upon the transgenic animals' survival; the response of treated transgenic animals and untreated transgenic animals is compared using any of the assays described herein (in addition, treated and untreated non-transgenic animals may be included as controls). A compound which causes an improvement in any parameter associated with heart failure when used in the screening methods of the instant invention may thereby be identified as a therapeutic compound.

The term "sample" in the present specification and claims is used in its broadest sense. On the one hand it is meant to include a specimen or culture (e.g., microbiological cultures). On the other hand, it is meant to include both biological and environmental samples.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water, and industrial samples, as well as samples obtained from food and dairy processing instruments, apparatus, equipment, utensils, disposable, and non-disposable items. These examples are not to be construed as limiting the sample types applicable to the present invention.

The phrase "at least one adenovirus gene coding region" refers to a nucleotide sequence containing more than one adenovirus gene coding sequence. A "helper adenovirus" or "helper virus" refers to an adenovirus which is replication-competent in a particular host cell (the host may provide Ad gene products such as E1 proteins), this replication-competent virus is used to supply in trans functions (e.g., proteins) which are lacking in a second replication-incompetent virus; the first replication-competent virus is said to "help" the second replication-incompetent virus thereby permitting the propagation of the second viral genome in the cell containing the helper and second viruses.

DETAILED DESCRIPTION OF THE INVENTION

The thin filament regulatory protein troponin I (TnI) plays a central role in ischemia-mediated contractile dysfunction. TnI is the inhibitory subunit of the troponin complex that functions as a molecular switch by shuttling between actin (diastole) and troponin C (systole) in a calcium-dependent manner (See, e.g., Solaro and Rarick, Circ Res 83:471 (1998); Westfall and Metzger, News Phyiol Sci 16:278 (2001)). TnI regulates cardiac contraction in an isoform-specific manner by increasing or decreasing the calcium responsiveness of the myofilament depending on the intracellular milieu and its phosphorylation states (See, e.g., Solaro and Rarick, Circ Res 83:471 (1998); Metzger and Westfall Circ Res 94:1462004). During acidosis in particular, expression of the fetal cardiac isoform (slow skeletal TnI or ssTnI) renders cardiac muscle resistant to the detrimental effects of acidosis, relative to the adult cardiac isoform (cardiac TnI or cTnI) (See, e.g., Solaro et al., *Circ Res* 63:779 (1988); Hunkeler et al., Circ Res 69:1409 (1991)). What is needed is a treatment for heart failure or disease that enhances myofilament calcium sensitivity under acidic conditions by decreasing the pH sensitivity of TnI. Such a treatment would be beneficial in combating the profound depression in myocardial performance observed during and after ischemia.

Accordingly, the invention provides recombinant troponin I (TnI) protein and nucleic acids encoding recombinant TnI that preserves normal function during ischemia and reperfusion. In particular, the present invention provides nucleic acids encoding gain of function TnI proteins (e.g., cTnIA164H), vectors containing such nucleic acids, host cells containing such vectors, transgenic animals carrying a gain of function TnI protein (e.g., a cTnIA164H transgene), and therapeutic agents (e.g., comprising recombinant TnI, TnI analogues, synthetic TnI, or the like) or agents for gene therapy of heart failure or disease.

TnI isoform and chimera structure-function studies in cardiac myocytes have localized the pH sensitivity domain to a large C-terminal domain of TnI (See, e.g., Westfall et al., Circ Res 86:470 (2000); Westfall et al., J Biol Chem 274:22508 (1999); Westfall et al., Circ Res 91:525 (2002)). In order to identify a more limited domain or residue that confers pH sensitivity, a series of ssTnI mutants were generated. In some embodiments, the present invention provides gain of function TnI mutants, incorporating conserved residue substitutions from cTnI (See, e.g., Example 2, FIG. 2). In some embodiments, the invention provides an isolated nucleic acid sequence that encodes a gain of function TnI protein, the protein having an amino acid substitution of histidine for alanine (See, e.g., Example 3, FIG. 2). In some embodiments, the invention provides an isolated nucleic acid sequence that encodes a gain of function TnI protein having an amino acid substitution, wherein a natural or synthetic, charged amino acid (e.g., histidine) replaces alanine at codon 163 (monkey, human or cat), 164 (rat, cow, mouse or dog) or 158 (horse) of TnI.

Without being bound to any theory (an understanding of the mechanism is not necessary to practice the present invention, and the present invention is not limited to any particular mechanism), the preservation of contractile force by the gain of function mutants (e.g., cTnIA164H) provided herein are explainable by the single histidine substitution's effects on myofilament calcium responsiveness. For example, during acidosis and acute ischemia, the myofilament calcium sensitivity is reduced. Likewise, post-ischemic contractile dysfunction, often referred to as myocardial stunning (See, e.g., Braunwald and Kloner Circulation 66:1146 (1982)) is characterized by a diminution in calcium responsiveness (See, e.g., Gao et al., Circ Res 78:455 (1996); Hofmann et al., Circ Res 72:50. (1993)). Thus, although an understanding of the mechanism is not necessary to practice the present invention and the present invention is not limited to any particular mechanism of action, in some embodiments, it is contemplated that the gain of function TnI proteins of the present invention function via a mechanism that preserves normal LVEDP during acidosis and reduces the degree of contracture, or diastolic chamber stiffness, during ischemia and reperfusion. Contracture, which renders cardiomyocytes susceptible to mechanical damage and ultimately necrosis, occurs as a result of either intracellular calcium overload, energy depletion, or both (See, e.g., Piper et al., Ann Thorac Surg 75:S644 (2003); Steenbergen et al., Circ Res 66:135 (1990); Varma et al., Am J Physiol 284:H758 (2003)). Ventricular reperfusion arrhythmias, which were markedly suppressed in gain of function TnI transgenic hearts, are also associated with elevated diastolic calcium levels (See, e.g., del Monte et al., Proc Natl Acad Sci 101:5622 (2004)). Therefore, while knowledge of a particular mechanism is not needed to practice the current invention, it is contemplated that the secondary effects of expression of gain of function cTnI (e.g., cTnIA164H), or other charged amino acid substitutions for alanine, on either calcium cycling or substrate utilization are responsible for its favorable gain of function effects during ischemia/reperfusion injury.

A. Nucleic Acids Encoding TnI Proteins

The present invention contemplates the use of nucleic acids encoding gain of function TnI proteins to treat heart failure. The present invention is not limited to the use of nucleic acid encoding any particular gain of function TnI protein. Indeed, the use of a variety of gain of function TnI proteins are contemplated. Gain of function TnI proteins that find use in the present invention include, but are not limited to, those mutants described in FIGS. 1 and 2. In a preferred embodiment, the gain of function TnI nucleic acid encodes a TnIA164H protein. In some embodiments, the nucleic acids are linked to vectors (e.g., vectors that contain tissue specific, and/or inducible promoters).

In some embodiments, TnI of the present invention may be synthetically constructed, expressed in mammalian cells, insects, bacteria, yeast, reptiles or fungi, recombinantly expressed from a cell culture or higher recombinant species such as a mouse, or otherwise. This would include activity-retaining (e.g., gain of function activity) synthetic construction including synthetic peptides and polypeptides or recombinant expression of portions of TnI responsible for gain of function activity, including chimeric proteins (e.g., including the gain of function mutations described herein).

B. Delivery of Gain of Function TnI Proteins to Cardiac Myocytes

The present invention contemplates the delivery of exogenous nucleic acids encoding gain of function TnI proteins, or the delivery of proteins themselves (e.g., recombinant gain of function TnI, synthetic gain of function TnI, gain of function TnI analogues, etc.) to cardiac myocytes via any suitable method. In preferred embodiments, nucleic acids are delivered as vectors. The present invention is not limited to any particular vector. Indeed, a variety of vectors may be used to deliver the nucleic acids.

In preferred embodiments, the nucleic acid encoding a gain of function TnI protein is delivered via an adenovirus vector. (See e.g., Westfall et al., Meth. Cell Biol. 32:307-322 (1998); and U.S. Pat. Nos. 6,451,596, 6,083,750, 6,063,622, 6,057, 158, or 5,994,132, all of which are herein incorporated by reference). In some embodiments, recombinant adenovirus vectors are constructed by homologous recombination of a shuttle vector containing a nucleic acid encoding a calcium binding protein and the full-length adenovirus DNA following co-transfection into a human embryonic kidney (i.e., HEK 293) cell line. In some embodiments, the full-length adenovirus DNA is provided from pJM17 which is a 0-100 map unit (m.u.) derivative of adenovirus serotype (Ad5) that contains a partial deletion in the E3 region and a 4.3-kb pBRX insert at 3.7 m.u. (See e.g., Graham and Prevec, Manipulation of Adenovirus Vectors, in Gene Transfer and Expression Protocols, E. J. Murray ed., Humana, Clifton, N.J. (1991); and Becker et al., Use of Recombinant Adenovirus for Metabolic Engineering of Mammalian Cells, in Methods in Cell Biology, Vol 43 M. G. Roth ed., Academic Press, N.Y. (1994); Grahm and Prevec, Methods Mol. Biol. 7, 109 (1991)). In some particularly preferred embodiments, the shuttle vector comprises 0-1 m.u. and 9-16 m.u. of the Ad5 genome flanking an expression cassette containing the nucleic acid encoding a calcium binding protein. In some embodiments, homologous recombination results in the replacement of the pBRX insert and E1 region, making the recombinant adenovirus capable of being packaged but replication defective.

In other embodiments, the nucleic acid encoding a gain of function TnI protein is delivered to myocytes via an adeno-associated vector (AAV). In some particularly preferred embodiments, the AAV vector integrates into the genome of the cardiac myocyte. A number of AAV vectors which have been developed for gene therapy are useful in the present invention (See e.g., U.S. Pat. Nos. 5,173,414; 5,139,941; and 5,843,742; PCT publications WO92/01070 and WO93/03769; Lebkowski et al., Mol. Cell. Biol. 8:3988-3996 (1988); Carter, Curr. Opin. Biotech. 3:533-39, (1992); Muzyczka, Curr. Top, Microbiol. Immunol. 158:97-129, (1994); Kotin, Human Gene Ther. 5:793-801, (1994); Shelling and Smith, Gene Ther. 1:165-69, (1994); Zhou et al., J. Exp. Med. 179:1867-1875, (1994); U.S. Pat. Nos. 6,451,596, 6,083,750, 6,063,622, 6,057,158, or 5,994,132; Ferrari et al., Nature Med. 3(11):1295-97, (1997); and Gregorevic et al., Nature. Med. 10(8): 828 (2004), each of which is incorporated herein by reference in its entirety).

In still other embodiments, the nucleic acid encoding a gain of function TnI protein is delivered via a liposome or naked DNA plasmids. In some particularly preferred embodiments, the liposome is a cationic liposome (See e.g., U.S. Pat. Nos. 5,908,777 and 5,676,954 each incorporated herein by reference in their entireties; Hug and Sleight, Biochim. Biophys. Acta. 1097:1-17, (1991); Straubinger et al., in Methods of Enzymology, Vol. 101 pp. 512-527 (1993); Felgner et al., Nature 337:387-388, (1989); and Felgner et al., PNAS (1987) 84:7413-7416) (1987)). An example of a commercially available cationic liposome carrier useful in the present invention is LIPOFECTIN (Bethesda Research Laboratories Life Technologies, Inc., Gaithersburg Md.).

In some preferred embodiments of the present invention, the vector further includes a suitable promoter and enhancer, and also any necessary ribosome binding sites, polyadenylation site, splice donor and acceptor sites, transcriptional termination sequences, and 5' flanking nontranscribed sequences. In other embodiments, DNA sequences derived from the SV40 splice, and polyadenylation sites may be used to provide the required non-transcribed genetic elements.

In some embodiments of the present invention, the DNA sequence in the expression vector is operatively linked to an appropriate expression control sequence(s) (e.g., promoter) to direct mRNA synthesis. In some embodiments, the promoter is preferably the cytomegalovirus (CMV) promoter. In other embodiments, a cardiac specific promoter (e.g., α-MyHC and β-MyHC promoter (See e.g., Palermo et al., Circul. Res. 78(3):504-509, (1996)) is utilized. Other promoters useful in the present invention include, but are not limited to, the LTR or SV40 promoter, the $E.\ coli.$ lac or trp, the phage lambda $P_L$ and $P_R$, T3 and T7 promoters, HSV thymidine kinase, and mouse metallothionein-I promoters and other promoters known to control expression of genes in prokaryotic or eukaryotic cells or their viruses. In some embodiments, recombinant expression vectors include selectable markers permitting transformation of the host cell (e.g. dihydrofolate reductase or neomycin resistance for eukaryotic cell culture). In some embodiments, the promoter is a tissue specific and/or inducible promoter.

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription; Enhancers useful in the present invention include, but are not limited to, the SV40 enhancer (e.g., 100 to 270 base pairs on the late side of the replication origin), a cytomegalovirus early promoter enhancer, the polyoma enhancer (e.g., on the late side of the replication origin), and adenovirus enhancers.

In other embodiments, the expression vector also contains a ribosome binding site for translation initiation and a transcription terminator. In still other embodiments of the present invention, the vector includes appropriate sequences for amplifying expression.

C. TnI Transgenic Animals

Figure 2:
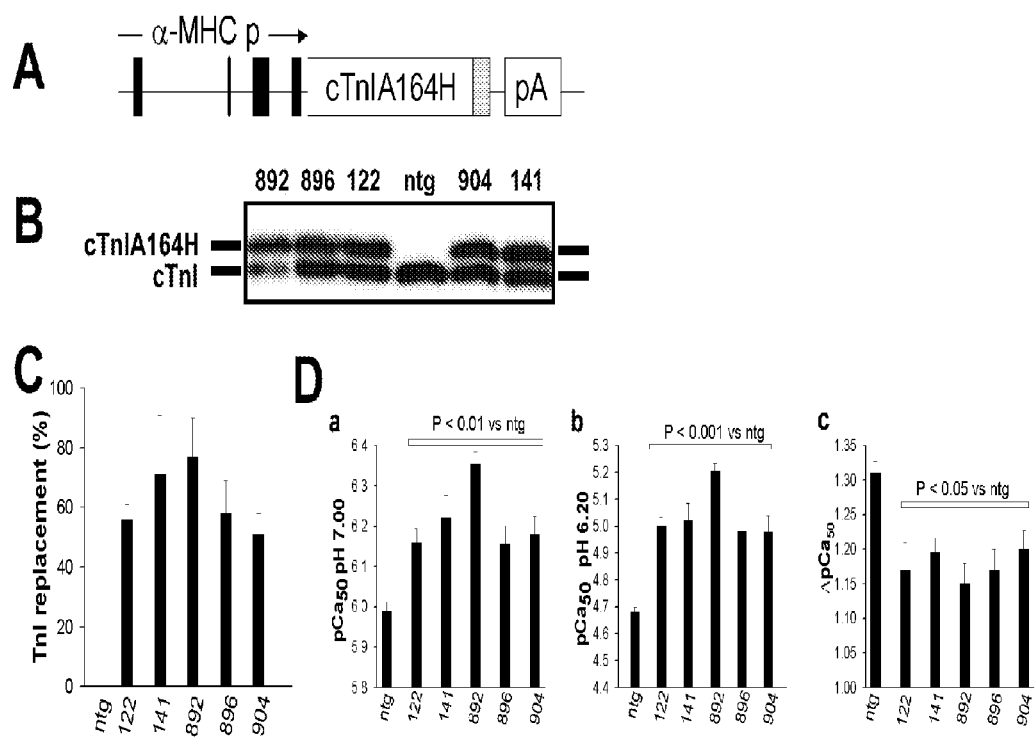
FIG. 2 depicts (A) cardiac TnIA164H transgene, (B and C) stoichiometric replacement of cTnI in five independent transgenic lines of mice, and (D) isolated cardiac myocyte isometric contractile function.
Figure 3:
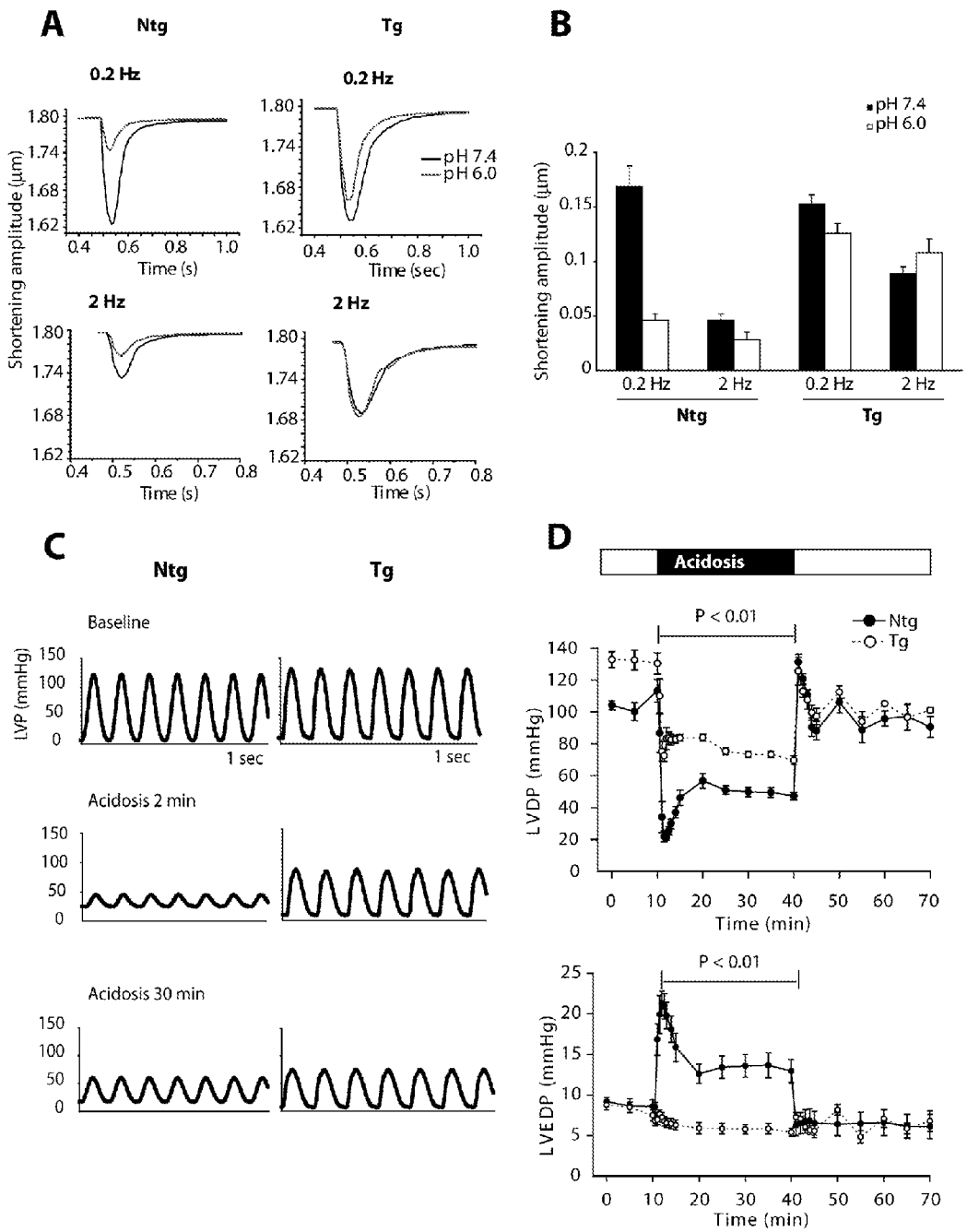
FIG. 3 depicts preservation of contractility during acidosis in cTnIA164H transgenic mice.
Figure 4:
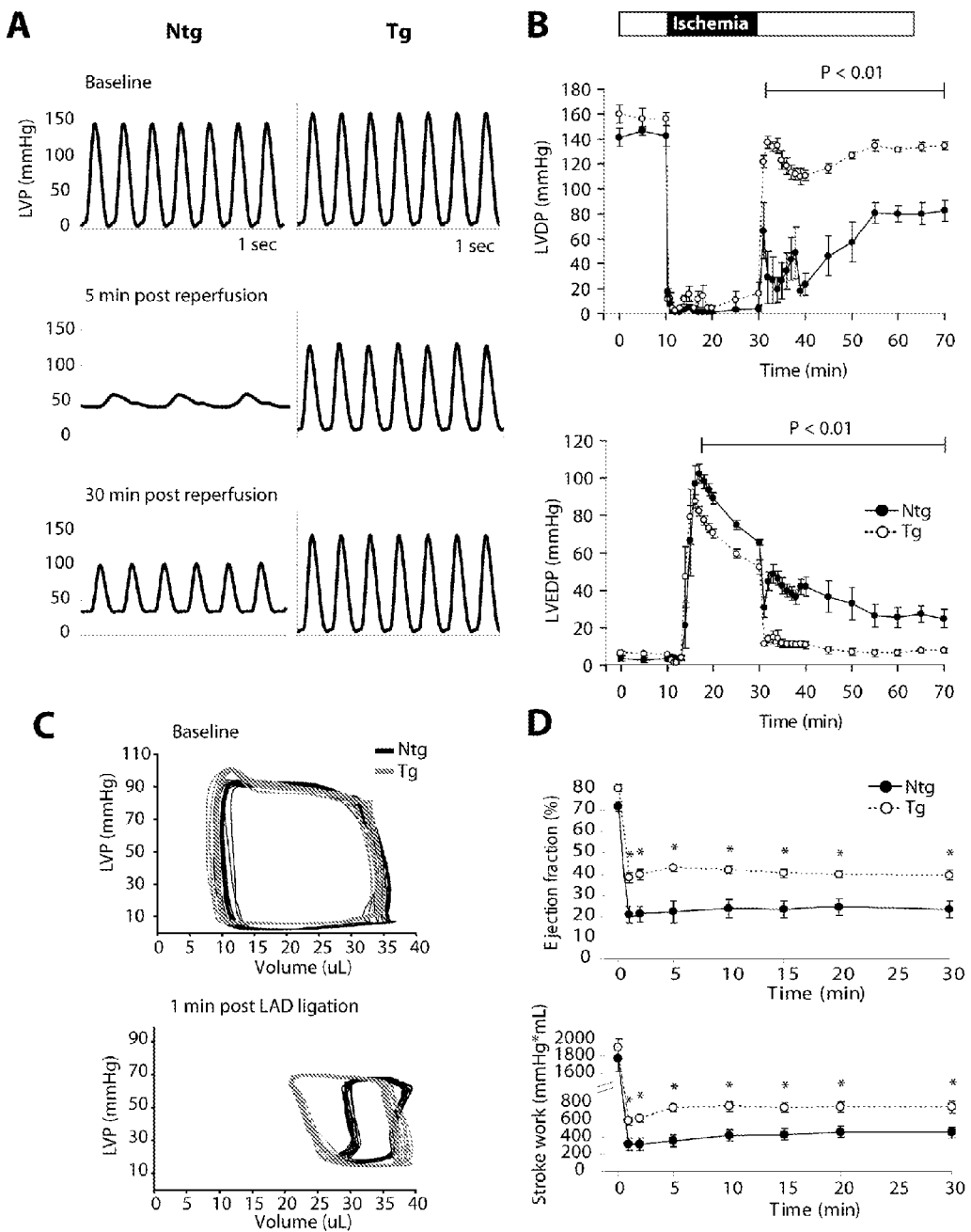
FIG. 4 depicts hemodynamics during ischemia and reperfusion (isolated heart) (A and B) and acute LCA ligation in vivo (C and D).

In some embodiments, the invention provides a transgenic animal carrying a gain of function TnI nucleic acid (e.g., a cTnIA164H transgene) under the control of a promoter sequence, wherein the gain of function TnI transgene is expressed in cardiac cells (See, e.g., Example 3, FIGS. 2-4). In some embodiments, the promoter sequence is the α-myosin heavy chain promoter. In a preferred embodiment, the transgenic animal is a mouse. The present invention is not limited by the type of transgenic animal. Indeed, a variety of animals are contemplated to be useful in the present invention including, but not limited to, pigs, dogs, monkeys, cats, rats, and rabbits. In some embodiments, the transgenic animals find use in research, drug screening and therapy optimization.

D. Heart Failure Treatment with Mutant TnI Proteins

The present invention provides treatment of heart failure through the expression in, or delivery to, cardiac myocytes gain of function TnI proteins (e.g., from exogenous nucleic acids, or from gain of function recombinant TnI, or analogues thereof).

Although an understanding of the mechanism is not necessary to practice the present invention and the present invention is not limited to any particular mechanism of action, in some embodiments, gain of function TnI proteins (e.g., provided to cardiac myocytes or expressed therein (e.g., using expression vectors described herein)) preserves myofibril contractile force during acidosis.

Accordingly, the present invention provides methods for treating heart failure due to ischemia induced acidosis. In some embodiments of the present invention, the vectors described above are used to deliver exogenous nucleic acid encoding a gain of function TnI protein to cardiac myocytes (e.g., transfect the cardiac myocytes). In some embodiments, the vectors (e.g., liposome delivered vectors or AAV vectors) are administered directly to the left ventricular wall of the heart or in vivo by intravenous injection. In preferred embodiments, an adenovirus vector containing an expression cassette encoding a gain of function TnI protein (e.g., TnIA164H) is injected into the left ventricle. In some preferred embodiments, the TnI protein is expressed from the nucleic acid so that intracellular levels of the TnI protein are detectable (e.g., via a Western blot). In particularly preferred embodiments, the gain of function TnI proteins (e.g., recombinant proteins or nucleic acid encoding the same provided to the left ventricular wall of the heart) preserve normal left ventricular systolic and end-diastolic pressures (LVEDP) during acidosis (See, e.g., Examples 4 and 5, FIGS. 3 and 4).

E. Drug Screens

It is also contemplated that the cardiac myocytes comprising an exogenous nucleic acid encoding a gain of function TnI protein are used in a variety of drug screening assays. In some embodiments, the cardiac myocytes are used as a control for the screening of potential cardioactive reagents and therapeutics. In some embodiments, cells expressing exogenous gain of function TnI proteins are used as a functional guide of robust improvement in cardiac left ventricular end-diastolic pressure.

In some preferred embodiments, cardiac myocytes expressing exogenous gain of function TnI (e.g., TnIA164H) transfected cardiac myocytes) and wild-type cardiac myocytes are provided. In some embodiments, the transfected and wild-type cardiac myocytes are then exposed in vitro, ex vivo, or in vivo to an agent (e.g., drug or therapeutic agent) suspected of having a cardioactive effect.

In some preferred embodiments, the LVEDP during acidosis in the transfected and wild-type cardiac myocytes is assayed. In some embodiments, agents that increase the LVEDP in the wild-type myocytes to levels comparable to those observed in non-treated, transfected myocytes are chosen for further testing (e.g., in vivo, ex vivo or in vitro) for the treatment of heart failure. In other embodiments, agents that decrease the LVEDP in transfected or wild-type cardiac myocytes are identified as being agents that potentially cause or compound heart failure. In other preferred embodiments, animals expressing exogenous gain of function TnI (e.g., transgenic animals) in their cardiac myocytes and wild-type animals are provided so that the cardioactivity of agents may be assayed in vivo. In some embodiments, agents suspected of having a cardioactive effect are administered to the animals. In some particularly preferred embodiments, these agents have been identified in the in vitro screen described above. In some embodiments, the LVEDP is calculated in treated and non-treated animals. In some embodiments, agents that cause an increase in the LVEDP comparable to that seen in non-treated, transfected animals are identified as candidates to treat heart failure. In other embodiments, agents that decrease the LVEDP in wild-type or transfected animals are identified as being materials that potentially cause or compound heart failure.

F. Therapeutic Agents and Agents for Gene Therapy for Heart Failure

In some embodiments, the present invention utilizes gene replacement therapy approaches to deliver and express gain of function TnI proteins (e.g., TnIA164H) in myocytes. Using these methods, expression of gain of function TnI proteins from exogenous nucleic acids results in enhanced myofilament calcium sensitivity at normal and acidic pH in cardiac myocytes from both normal and diseased (e.g., ischemic) mouse hearts (See, e.g., Examples 4 and 5). Consequently, gain of function TnI expression in cardiac tissue represents an important new technology for the treatment of left ventricular systolic and diastolic pressure dysfunction in response to acidosis in subjects with heart failure. Additionally, the present invention provides in vitro studies of TnI expressing cardiac myocytes useful as a screen (e.g., in vitro) for the development and testing of novel cardioactive drugs and therapeutics.

Since the proteins and the genes of the present invention have left ventricular pressure enhancing, LVEDP stabilizing activity, they are useful as therapeutic agents and as agents for gene therapy, respectively, for heart failure. In some embodiments of the present invention, the therapeutic agents or the agents for gene therapy of the present invention are administered to a subject orally or parenterally and systemically or locally (e.g., directly to heart tissues or cells). In some embodiments, the proteins (e.g., recombinant gain of function TnI or analogues thereof, synthetic gain of function TnI, etc), and genes find use in research applications (e.g., to study the contractile machinery of the heart) and therapeutic applications.

When the gain of function protein or the gene of the present invention is used as a therapeutic agent or an agent for gene therapy for heart failure, the application of the present invention is not limited by the underlying mechanism of heart failure. For example, the proteins or the genes may be used for heart failure caused by myocardial infarction, myofilament contractility abnormalities or any type of cardiomyopathy.

In preferred embodiments of the present invention, when the agent of the invention is administered orally, the agent may be formulated into a tablet, capsule, granule, powder, pill, troche, internal liquid agent, suspension, emulsion, syrup or the like. Alternatively, the therapeutic agent may be prepared into a dry product which is re-dissolved just before use. In preferred embodiments, when the therapeutic agent of the invention is administered parenterally, the agent may be formulated into an intravenous injection (including drops), intramuscular injection, intraperitoneal injection, subcutaneous injection, suppository, or the like. Injections are supplied in the form of unit dosage ampules or multidosage containers. These formulations may be prepared by conventional methods using appropriate excipients, fillers, binders, wetting agents, disintegrating agents, lubricating agents, surfactants, dispersants, buffers, preservatives, dissolution aids, antiseptics, flavoring/perfuming agents, analgesics, stabilizers, isotonicity inducing agents, etc. conventionally used in pharmaceutical preparations.

Each of the above-described formulations may contain pharmaceutically acceptable carriers or additives. Specific examples of such carriers or additives include water, pharmaceutically acceptable organic solvents, collagen, polyvinyl alcohol, polyvinylpyrrolidone, carboxyvinyl polymers, sodium alginate, water-soluble dextran, sodium carboxymethyl amylose, pectin, xanthan gum, gum arabic, casein, gelatin, agar, glycerol, propylene glycol, polyethylene glycol, Vaseline, paraffin, stearyl alcohol, stearic acid, human serum albumin, mannitol, sorbitol and lactose. One or a plurality of these additives are selected or combined appropriately depending of the form of the preparation.

The dosage levels of the therapeutic agent of the invention will vary depending on the age of the subject, the route of administration and the number of times of administration and may be varied in a wide range. When an effective amount of the protein of the invention is administered in combination with an appropriate diluent and a pharmaceutically acceptable carrier, the effective amount of the protein can be in the range from 0.01 to 1000 mg/kg per administration, although other amounts are contemplated, where appropriate. One skilled in the art is capable of determining the therapeutically effective amount appropriate any given circumstances. In some embodiments, the therapeutic agent is administered once a day or in several dosages per day for at least one day.

In some embodiments of the present invention, when the gain of function gene of the invention is used as an agent for therapy (e.g., to treat or prevent disease, for example, as gene therapy) for heart failure, a gain of function gene or protein of the invention may be directly administered by injection. Alternatively, a vector incorporating the gain of function gene of the invention may be administered. Specific examples of a suitable vector for this purpose include an adenovirus vector, adeno-associated virus vector, herpes virus vector, vaccinia virus vector and retrovirus vector. The gain of function gene of the invention can be administered efficiently by using such a virus vector. Alternatively, the gene of the invention may be enclosed in phospholipid vesicles such as liposomes, and the resultant liposomes may be administered to the subject. Briefly, since liposomes are biodegradable material-containing closed vesicles, the gene of the invention is retained in the internal aqueous layer and the lipid bilayer of liposomes by mixing the gene with the liposomes (e.g., a liposome-gene complex). Subsequently, when this complex is cultured with cells, the gene in the complex is taken into the cells (e.g., lipofection). Then, the resultant cells may be administered by the methods described below.

In some embodiments of the present invention, as a method for administering the agent for gene therapy of the invention, local administration to tissues of the central nervous system may be performed in addition to conventional systemic administration such as intravenous or intra-arterial administration. Further, an administration method combined with catheter techniques and surgical operations may also be employed.

The dosage levels of the agent for gene therapy of the invention vary depending on the age, sex and conditions of the subject, the route of administration, the number of times of administration, and the type of the formulation, among other considerations. One skilled in the art is capable of determining the therapeutically effective amount appropriate under any given circumstance. Usually, it is appropriate to administer the gene of the invention in an amount of 0.1-100 mg/adult body/day, although other concentrations are contemplated, where appropriate.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: g (grams); l or L (liters); .mu.g (micrograms); .mu.l (microliters); .mu.m (micrometers); .mu.M (micromolar); lmol (micromoles); mg (milligrams); ml (milliliters); mm (millimeters); mM (millimolar); mmol (millimoles); M (molar); mol (moles); ng (nanograms); nm (nanometers); nmol (nanomoles); N (normal); pmol (picomoles); Hz (hertz); Stratagene (Stratagene, La Jolla, Calif.); Clontech (BD Biosciences-Clontech, Palo Alto, Calif.); Metamorph (Universal Imaging Corp., Downingtown, Pa.); and Ionoptix (Ionoptix, Milton, Mass.).

Example 1

Materials and Methods

TnI Substitutions and Viral Vector Construction:

Wild-type cTnI and ssTnI cDNAs and cTnI with a FLAG epitope on the C-terminus (Michele et al., J Cell Biol 145: 1483 (1999)) were used to construct the gain of function A164H substitution. A pGEM-3Z vector containing cTnI or ssTnI, and the QuikChange mutagenesis kit (Stratagene) were used to generate substitutions in cTnI and ssTnI. The primers used for mutagenesis of cTnI to cTnIA164H removed an Xma1 site and were 5'-ggcactactggggacccggcacaaggaatccttggacctg-3' (sense) (SEQ ID NO: 1) and 5'-caggtccaaggattccttgtgccgggtccccagtagtgcc-3' (antisense) (SEQ ID NO: 2). The mutants constructed from wild-type ssTnI included ssTnIR125Q, ssTnIH132A, ssTnIV134E, and ssTnIR125Q/H132A/V134E (ssTnIQAE; QAETAT). A unique Ava I site was introduced into ssTnIR125Q, ssTnIH132A, and ssTnIV134E, and this site was subsequently removed from ssTnIR125Q to construct the ssTnIQAE mutant. The primers used for mutagenesis to ssTnIR125Q were 5'-cgccatgctccaggccctactcgggtcaaacacaag-3' (sense) (SEQ ID NO: 3) and 5-cttgtgtttgaccgagtagggcctggagcatggcg-3' (antisense) (SEQ ID NO: 4) and 5'-caggccctactgggttccaaagccaaggaatccatggatctgcg-3' (sense) (SEQ ID NO: 5) and 5'-ccgcagatccatggattccttggctttgaacccagtagggcctg-3' (antisense) (SEQ ID NO: 6) for ssTnIQAE prepared from ssTnIR125Q. Primers for ssTnIH132A were 5'-cgagcccta ctcgggtccaaagccaaggtgtccatgg-3' (sense) (SEQ ID NO: 7) and ccatggacaccttggctttggaccgagtagggctcg-3' (antisense) (SEQ ID NO: 8), and primers for ssTnIV134E were 5'-cgagc-cctactcgggtccaaacacaaggaatccatggatctg-3' (sense) (SEQ ID NO: 9) and 5'-cagatccatggattccttgtgtttggacccgagtagggctcg-3' (antisense) (SEQ ID NO: 10). Primers were then extended using Pfu DNA polymerase and methylated parental DNA was subsequently digested with Dpn I. DNA containing each mutation was transformed into competent bacterial cells. Mutated DNA with appropriate restriction enzyme sites were sequenced prior to ligation of mutant cTnI and ssTnI cDNA into Ad5 viral shuttle vectors. All DNA sequences were verified by overlapping sequence runs. Recombinant vectors were produced and purified as described previously (Westfall et al., Methods Cell Biol 52:307 (1997)).

Adult Rat Cardiac Myocyte Isolation and Adenoviral Gene Transfer.

Adult rat cardiac myocytes were isolated by enzymatic digestion and plated on laminin-coated coverslips in Dulbecco's modified Eagle's medium (DMEM) containing 5% fetal bovine serum, 50 units/mL penicillin, and 50 µg/mL streptomycin (P/S) as described previously Westfall et al., Proc Natl Acad Sci 94:5444 (1997). After 2 hours, media was replaced with adenovirus diluted in serum-free DMEM+P/S. Serum-free media was added after an hour incubation with adenovirus, and media was changed the day after adding virus and then every other day.

Transgenic Mice.

The transgenic constructs utilized the α-MyHC promoter to drive expression of rat cTnI A164H Flag in the adult murine heart. The mutagenesis of rat cTnI A164H was done using Site-Directed Mutagenesis Kit (Clontech) and the constructs were verified by DNA sequencing. Constructs were microinjected into C57BL/6xSJL $F_2$ fertilized eggs and implanted in pseudopregnant females. Transgenes in mouse genomic DNA were detected by PCR using the following pairs: 5'AGACAGATCCCTCCTATCTC 3' (SEQ ID NO: 11) in the MyHC promoter and 5'GTGATGTTCTTGGTGACTTTT 3' (SEQ ID NO: 12) complimentary to the rat cTnI. Transgenic founders were backcrossed to C57BL/6 mice. Five lines carrying the rat cTnI A164H Flag transgene were established. For all experiments described, F1 and F2 male and female progeny from a cross of SJL and C57BL/6 strains were studied and ntg littermates were used as controls.

Isometric Tension Measurements in Permeabilized Myocytes.

Cardiac myocytes were isolated by mechanical disruption and permeabilized in 0.2% Triton X-100. $Ca^{2+}$-activated tension was measured in single myocytes attached to a force transducer via glass micropipets at pH 7.0 and pH 6.2 as described (Westfall et al., Circ Res 86:470 (2000)). Tension-pCa (-log molar ($Ca^{2+}$)) relationships were constructed by expressing tension at various submaximal $Ca^{2+}$ concentrations as a fraction of tension at maximal activation (pCa=4.0). The $Ca^{2+}$ concentration required for half maximal activation was expressed as $pCa_{50}$.

Adult Mouse Myocyte Isolation, Morphometric Analysis, and Functional Measurements.

Adult mouse cardiac myocyte isolation was performed as described previously (Coutu et al, Circ Res 94:1235 (2004). Typically, 5-10×10$^5$ rod-shaped cells were obtained from a single mouse heart. For morphometric analysis, cells were plated on laminin-coated coverslips in the presence and absence of 10 mM 2,3-butanedionemonoxime (BDM). Microscopic images were recorded and analyzed for cell area using morphometrics software (Metamorph). For functional measurements, intact myocytes were incubated in media 199 supplemented with P/S, 10 mM HEPES, 0.2 mg/mL bovine serum albumin and 10 nM glutathione. Dynamic sarcomere shortening and relengthening was measured using a high intensity video-based detection system (Ionoptix, Milton, Mass.) at 37° C. at a pacing frequency of 0.2 Hz as described previously (Coutu et al, Circ Res 94:1235 (2004); Coutu and Metzger Biophys J 82:2565 (2002)).

Echocardiography.

Mice were anesthetized with 1% inhaled isoflurane in oxygen and echocardiograms were performed using a GE Vivid 7 and an S10 MHz phased array transducer. Systolic and diastolic dimensions and wall thickness were measured in M-mode in the parastemal short axis view at the level of the papillary muscles (Michele et al., Circ Res 92:255 (2002); Skatkowski et al., J Clin Invest 107:191 (2001)). In vivo acceleration of heart relaxation performance by Parvalbumin gene delivery. Fractional shortening and ejection fraction were calculated from the M-mode parastemal short axis view (Michele et al., Circ Res 92:255 (2002)). Diastolic function was assessed by conventional pulsed-wave spectral Doppler analysis of mitral valve inflow patterns (early (E) and late (A) filling waves). Doppler tissue imaging (DTI) was used to measure the early ($E_a$) and late ($A_a$) diastolic tissue velocities of the mitral annulus.

Conductance Micromanometry.

In vivo hemodynamic measurements were obtained using conductance micromanometry as previously performed by our laboratory (Skatkowski et al., J Clin Invest 107:191 (2001)) and adapted to the mouse. A 1.4 French Millar pressure catheter was inserted into the apex of the LV under direct visualization. All measurements were collected on line at 1 kHz.

Isolated Heart Model (Langendorff) and Experimental Protocols.

Isolated, isovolumic-contracting mouse hearts were retrograde-perfused with a standard Krebs-Henseleit buffer (KHB) equilibrated with 95% $O_2$/5% $CO_2$ (pH 7.4) at a constant pressure of 80 mmHg, and paced at 7 Hz. Left ventricular pressure was monitored by means of a water-filled polyvinyl chloride balloon connected to a pressure transducer (Yet et al., Circ Res 89:168 (2001); Headrick et al., Experimental Physiology 86.6:703 (2001). For all experimental protocols, an initial 10 minute period was allowed for stabilization. For the acidosis protocol, the perfusion was rapidly switched to KHB equilibrated with a hypercarbic gas mixture (80% $O_2$/20% $CO_2$) in order to attain an acidic pH (pH 6.8) (Mundina-Weilenmann et al., Am J Physiol 39:C107 (1996). The duration of hypercarbic perfusion was 30 min, followed by another 30 min at physiologic perfusion. For the ischemia and reperfusion protocol, after the initial 10 minutes, the perfusion line was clamped for 20 minutes, followed by a 40 minute period of reperfusion. Pacing was discontinued one minute after cessation of flow and reinitiated during reperfusion. Left ventricular pressure measurements and electrocardiograms were collected on-line at a sample rate of 500 µs. Data analysis was performed using ADInstruments software (Chart for Windows, version 4.2.3).

Hemodynamic Measurements During Acute Ischemia In Vivo.

Mice were sedated with intraperitoneal sodium pentobarbital (45 mg/kg), intubated orally, and ventilated via a pressure-controlled ventilator with 1% isoflurane in 100% oxygen. The heart was exposed via a left thoracotomy, and a 7-0 silk suture was placed around the proximal portion of the left coronary artery (LCA) 1-2 mm from the left atrium, but not tied. The chest was filled with warn sterile saline to evacuate air and the incision was closed using 5-0 silk suture. The mice were recovered overnight. The following day, conductance micromanometry was performed as described above, with the Millar catheter placed through the LV apex. Once baseline measurements were obtained, the suture around the LCA was tied to occlude blood flow. Proper suture location was confirmed by the development of myocardial pallor. Hemodynamic measurements were recorded continuously for 30 minutes after LCA ligation.

Statistical Analysis:

Unless otherwise stated, all results are expressed as a mean A SEM. Comparison of continuous variables was performed using unpaired t-tests, or one-way analysis of variance (ANOVA) with Tukey post-hoc between-group comparisons. Paired t-tests were used to compare pre- and post-treatment values (as with addition of PKA or isoproterenol in the isolated myocyte studies). Two-way ANOVA with repeated measures with Tukey post-hoc between-group comparisons was used to analyze data from the isolated heart and in vivo ischemia experiments.

Example 2

Characterization of Troponin I (TnI) Residues Conferring pH Sensitivity

To address whether a limited domain or residue can confer pH sensitivity, a series of ssTnI mutants incorporating 3-6 conserved residue substitutions from cTnI, designated QAETAT and QAE ssTnI mutants, were constructed (See, e.g., FIG. 1). Upon gene transfer to adult cardiac myocytes from rats, the mutant TnIs stoichiometrically replaced >90% of endogenous cTnI, with no other detected changes in sarcomere protein expression (See, e.g., FIG. 1B). These cardiac TnI substitutions into ssTnI to form ssTnIQAE fully converted the ssTnI contractile phenotype to the cTnI phenotype as assessed by single myocyte recordings of isometric tension at varied steady-state levels of calcium activation (See, e.g., FIG. 1C). This narrowed the pH sensitivity domain to 3 amino acids. These amino acids are located in helixes 3 and 4 in TnI, which are predicted to act as an important molecular switch domain that toggles between actin and troponin C in the presence of calcium (Takeda et al., Nature 424:35 (2003); Gasmi-Seabrook et al., Biochemistry 38:14432 (1999); Tripet et al., J Mol Biol 271:728 (1997)). Subsequent single residue substitutions in ssTnI showed that histidine at position 132, but not valine 134 or arginine 125, fully accounted for the TnI isoform dependence of the pH sensitivity phenotype (See, e.g., FIG. 1D). Substituting histidine for alanine at codon 164 in cTnI resulted in a significant gain-of-calcium activated tension development, most dramatically under acidic pH conditions (See, e.g., Example 3).

Example 3

Generation of cTnIA164H Transgenic Mice

Five independent lines of transgenic mice were generated using the α-myosin heavy chain promotor to direct cardiac-restricted expression of the cTnIA164H cDNA (See, e.g., FIG. 2). A C-terminal Flag epitope was used to aid in detection of cTnIA164H. Gene transfer studies showed that the Flag epitope did not alter the calcium or pH sensitivity of isometric force in cardiac myocytes. All transgenic (tg) lines were viable and reproductively fit. Stoichiometric replacement of native cTnI by cTnIA164H varied between 51-83% among the five transgenic lines (See, e.g., FIGS. 2B and 2C).

Sarcomeric localization of cTnIA164H was confirmed by confocal projection imaging of indirect immunofluorescently-labeled myocardial sections. Correspondingly, there was a marked gain-of-function in isometric tension recordings in chemically permeabilized myocytes that was particularly dramatic at pH 6.20, and correlated with the extent of TnI replacement (See, e.g., FIG. 2D). In contrast to myocytes from transgenic mice expressing ssTnI in the heart (Fentzke et al., J Physiol 517.1:143 (1999)), cTnIA164H-expressing myocytes treated directly with the catalytic subunit of protein kinase A (PKA), retained myofilament desensitization to calcium activation of tension (Westfall et al., Am J Physiol 280:C324 (2001)). (pCa50: 6.25±0.05 (−PKA), 6.067±0.007 (+PKA, n=4, P<0.01).

Example 4

Functional Characterization of cTnIA164H Transgenic Mice

As line 892 showed the greatest TnI replacement and gain-of-function at the myocyte level, subsequent organ-level studies were focused on this line. Functional performance in cTnIA164H tg mice was assessed by measuring contractility and relaxation parameters in isolated, intact myocytes, and in the whole heart using echocardiography and conductance micromanometry. Transgenic myocytes demonstrated an increased shortening amplitude (0.199±0.05 vs. 0.169±0.05 μm, P<0.05) and slower relaxation (time to 50% relaxation 34.5±13.9 vs. 26.9±5.2 msec, n=18/group, P<0.05) compared to ntg myocytes. As predicted by a normal myofilament calcium desensitization to PKA in permeabilized myocytes, intact tg myocytes retained their ability to respond to β-stimulation. In response to 50 nM isoproterenol, a β-adrenergic agonist, contractility was increased (% of sarcomere length shortening: 11.0±2.5 to 16.7±3.6 in tg myocytes (n=18, p<0.05); 9.0±2.8 to 17.5±2.2 in ntg myocytes (n=18, P<0.05)) and relaxation was faster (time to 75% relaxation (sec): 0.0652±0.027 to 0.0524±0.0166 in tg (P<0.05); 0.0526±0.0151 to 0.0389±0.0069 in ntg (P<0.05)) in a qualitatively similar manner in myocytes from ntg and tg mice. Systolic function at the organ level was enhanced in tg mice, as demonstrated by both echocardiography (increased fractional shortening and ejection fraction (See, e.g., Table 1), and by in vivo hemodynamic measurements (increased ejection fraction and $dp/dt_{max}$ (See, e.g., Table 2). No significant differences were observed in parameters of diastolic function by echocardiography as measured by conventional Doppler and Doppler tissue imaging, but invasive hemodynamics revealed mild diastolic dysfunction (decreased $dp/dt_{min}$ and prolonged Tau). Transgenic hearts responded normally to the β-adrenergic agonist, dobutamine.

TABLE 1

Echocardiographic measurements.

|  | Ntg (n = 19) | Tg (n = 24) |
|---|---|---|
| IVS (mm) | 0.83 ± 0.03 | 0.84 ± 0.02 |
| PW (mm) | 0.77 ± 0.04 | 0.78 ± 0.02 |
| $LVD_d$ (mm) | 3.49 ± 0.09 | 3.08 ± 0.06* |
| $LVD_s$ (mm) | 2.15 ± 0.09 | 1.60 ± 0.07* |
| FS (%) | 39 ± 2 | 48 ± 1* |
| EF (%) | 76 ± 2 | 85 ± 1* |
| MV E (cm/s) | 91.3 ± 2.7 | 78.2 ± 3.3* |
| MV A (cm/s) | 59.2 ± 2.3 | 54.7 ± 2.2 |
| MV E:A | 1.52 ± 0.06 | 1.40 ± 0.05 |
| $E_a$ (cm/s) | 4.30 ± 0.25 | 3.89 ± 0.23 |

TABLE 1-continued

Echocardiographic measurements.

|  | Ntg (n = 19) | Tg (n = 24) |
|---|---|---|
| $E_a/A_a$ | 1.20 ± 0.10 | 1.08 ± 0.08 |
| IVRT (ms) | 12.58 ± 0.53 | 13.10 ± 0.66 |

IVS = intraventricular septal thickness,
PW = posterior wall thickness,
LVD = left ventricular dimension,
FS = fractional shortening,
EF = ejection fraction,
MV E and A = early and late mitral valve filling velocities,
$E_a$ and $A_a$ = early and late pulse-tissue doppler mitral annular velocities,
IVRT = isovolumic relaxation time.
Results are reported as mean ± SEM.
*P < 0.01.

Table 1. Echocardiographic Measurements
IVS=intraventricular septal thickness, PW=posterior wall thickness, LVD=left ventricular dimension, FS=fractional shortening, EF=ejection fraction, Mv E and A=early and late mitral valve filling velocities, $E_a$ and $A_a$=early and late pulse-tissue doppler mitral annular velocities, IVRT=isovolumic relaxation. Results are reported as mean±SEM. *P<0.01.

TABLE 2

In vivo conductance micromanometry measurements.

|  | Ntg (n = 13) | cTnI A164H (n = 15) |
|---|---|---|
| Heart rate (BPM) | 626 ± 7 | 605 ± 7 |
| $P_{max}$ (mmHg) | 96.4 ± 1.7 | 98.9 ± 1.3 |
| $dp/dt_{max}$ | 11345 ± 338 | 12859 ± 354293* |
| $dp/dt_{min}$ | (−) 10571 ± 177 | (−) 8791 ± 159* |
| EF (%) | 73 ± 1 | 80 ± 2* |
| Tau (Weiss) | 4.96 ± 0.14 | 6.28 ± 0.14* |

Tau = time constant of relaxation.
EF = ejection fraction.
Results are reported as mean ± SEM.
*P ≤ 0.01.

Table 2. In Vivo Conductance Micromanometry Measurements.
Tau=time constant of relaxation. EF=ejection fraction. Results are reported as mean±SEM. *P≤0.01.

Example 5

Contractility of Single Cells and Whole Organs from cTnIA164H Transgenic Mice

Bathing isolated nontransgenic myocytes in an acidic buffer caused a significant reduction in shortening amplitude. However, transgenic myocytes retained contractility under these acidic conditions (See, e.g., FIGS. 3A and 3B). Next, isolated mouse hearts were perfused with a physiologic buffer at pH 7.4 and 6.8, while keeping coronary perfusion pressure constant. In response to acidosis, ntg hearts developed a rapid decline in left ventricular systolic pressure (LVSP), accompanied by a simultaneous rise in LV end-diastolic pressures (LVEDP).

Transgenic expression of cTnI A164H afforded a marked protection from this drop in LVSP, and completely prevented the rise in LVEDP during acidosis (See, e.g., FIGS. 3C and 3D). Similar results were obtained during global ischemia and reperfusion. During 20 minutes of global no-flow ischemia, the degree of ischemic and post-ischemic contracture (characterized by a rise in left ventricular diastolic pressure) was significantly blunted in tg hearts expressing cTnIA164H compared to ntg hearts (See, e.g., FIGS. 4A and 4B). Post-ischemic contracture in ntg hearts occurred in the absence of relaxation abnormalities, as there was no difference between pre- and post-ischemic LV pressure decay, nor was post-ischemic LV pressure decay different between ntg and tg hearts. Expression of cTnIA164H also dramatically improved post-ischemic left ventricular developed pressure (See, e.g., FIGS. 4A and 4B) and myocardial recovery (84.9±3.5 vs. 57.4±4.6% of baseline, P<0.01) by the end of the 40 minute reperfusion period. This was accompanied by a significant suppression of ventricular arrhythmia duration during reperfusion (32±27 vs. 667±228 seconds, P<0.05).

The effects of cTnIA164H were also assessed in a model of regional ischemia in vivo, in which the left coronary artery was acutely ligated while simultaneously acquiring invasive hemodynamic measurements. Transgenic mice preserved contractility relative to their ntg counterparts during acute ischemia, as evidenced by a doubling of stroke work and ejection fraction (See, e.g., FIGS. 4C and 4D). These effects were evident immediately and were sustained throughout a 30 minute period of ischemia.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. An isolated nucleic acid sequence encoding a troponin I (TnI) protein comprising the amino acid sequence set forth in SEQ ID NO:13, wherein the Ala residue at position 43 is substituted with a His residue, and wherein said His residue permits said TnI protein to preserve contractile force during ischemic events, reperfusion injury, or other damage to cardiac tissues.

2. A recombinant expression vector comprising the nucleic acid of claim 1.

3. The recombinant expression vector of claim 2, wherein said expression vector is present in an adenoviral vector or an adeno-associated viral vector.

* * * * *

UNITED STATES PATENT AND TRADEMARK OFFICE
CERTIFICATE OF CORRECTION

PATENT NO. : 8,557,969 B2
APPLICATION NO. : 11/792216
DATED : October 15, 2013
INVENTOR(S) : Metzger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1450 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 14

<210> SEQ ID NO 1
<211> LENGTH: 40
<212> TYPE: DNA
<213> ORGANISM: Artificial Sequence
<220> FEATURE:
<223> OTHER INFORMATION: Synthetic

<400> SEQUENCE: 1
ggcactactg gggacccggc acaaggaatc cttggacctg                         40

```
<210> SEQ ID NO 2
<211> LENGTH: 40
<212> TYPE: DNA
<213> ORGANISM: Artificial Sequence
<220> FEATURE:
<223> OTHER INFORMATION: Synthetic

<400> SEQUENCE: 2
caggtccaag gattccttgt gccgggtccc cagtagtgcc                    40

<210> SEQ ID NO 3
<211> LENGTH: 37
<212> TYPE: DNA
<213> ORGANISM: Artificial Sequence
<220> FEATURE:
<223> OTHER INFORMATION: Synthetic

<400> SEQUENCE: 3
cgccatgctc caggccctac tcgggtccaa acacaag                       37

<210> SEQ ID NO 4
<211> LENGTH: 37
<212> TYPE: DNA
<213> ORGANISM: Artificial Sequence
<220> FEATURE:
<223> OTHER INFORMATION: Synthetic

<400> SEQUENCE: 4
cttgtgtttg gacccgagta gggcctggag catggcg                       37

<210> SEQ ID NO 5
<211> LENGTH: 44
<212> TYPE: DNA
<213> ORGANISM: Artificial Sequence
<220> FEATURE:
<223> OTHER INFORMATION: Synthetic

<400> SEQUENCE: 5
caggccctac tgggttccaa agccaaggaa tccatggatc tgcg               44

<210> SEQ ID NO 6
<211> LENGTH: 45
<212> TYPE: DNA
<213> ORGANISM: Artificial Sequence
<220> FEATURE:
<223> OTHER INFORMATION: Synthetic

<400> SEQUENCE: 6
ccgcagatcc atggattcct tggctttgga acccagtagg gcctg              45

<210> SEQ ID NO 7
<211> LENGTH: 37
<212> TYPE: DNA
<213> ORGANISM: Artificial Sequence
<220> FEATURE:
<223> OTHER INFORMATION: Synthetic

<400> SEQUENCE: 7
cgagccctac tcgggtccaa agccaaggtg tccatgg                       37

<210> SEQ ID NO 8
<211> LENGTH: 36
<212> TYPE: DNA
<213> ORGANISM: Artificial Sequence
<220> FEATURE:
<223> OTHER INFORMATION: Synthetic

<400> SEQUENCE: 8
```

```
ccatggacac cttggctttg gaccgagtag ggctcg                              36

<210> SEQ ID NO 9
<211> LENGTH: 42
<212> TYPE: DNA
<213> ORGANISM: Artificial Sequence
<220> FEATURE:
<223> OTHER INFORMATION: Synthetic

<400> SEQUENCE: 9
cgagccctac tcgggtccaa acacaaggaa tccatggatc tg                      42

<210> SEQ ID NO 10
<211> LENGTH: 42
<212> TYPE: DNA
<213> ORGANISM: Artificial Sequence
<220> FEATURE:
<223> OTHER INFORMATION: Synthetic

<400> SEQUENCE: 10
cagatccatg gattccttgt gtttggaccc gagtagggct cg                      42

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
agacagatcc ctcctatctc                                               20

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
gtgatgttct tggtgacttt t                                             21

<210> SEQ ID NO 13
<211> LENGTH: 52
<212> TYPE: PRT
<213> ORGANISM: Artificial Sequence
<220> FEATURE:
<223> OTHER INFORMATION: Synthetic

<400> SEQUENCE: 13

Asn Ile Thr Glu Ile Ala Asp Leu Thr Gln Lys Ile Phe Asp Leu Arg
1               5                  10                  15

Gly Lys Phe Lys Arg Pro Thr Leu Arg Arg Val Arg Ile Ser Ala Asp
            20                  25                  30

Ala Met Met Gln Ala Leu Leu Gly Ala Arg Ala Lys Glu Ser Leu Asp
        35                  40                  45

Leu Arg Ala His
    50

<210> SEQ ID NO 14
<211> LENGTH: 52
<212> TYPE: PRT
<213> ORGANISM: Artificial Sequence
<220> FEATURE:
<223> OTHER INFORMATION: Synthetic
```

```
<400> SEQUENCE: 14

Asn Thr Arg Glu Ile Lys Asp Leu Lys Leu Lys Val Leu Asp Leu Arg
1               5                   10                  15

Gly Lys Phe Lys Arg Pro Pro Leu Arg Arg Val Arg Val Ser Ala Asp
            20                  25                  30

Ala Met Leu Arg Ala Leu Leu Gly Ser Lys His Lys Val Ser Met Asp
        35                  40                  45

Leu Arg Ala Asn
    50
```